United States Patent [19]

Acher et al.

[11] Patent Number: 5,086,066
[45] Date of Patent: Feb. 4, 1992

[54] METHOD OF PROVIDING ANXIOLYTIC AND ANTIPSYCHOTIC TREATMENT WITH SUBSTITUTED BENZAMIDES

[75] Inventors: Jacques Acher, Itteville; Jean-Claude Monier, Lardy; Jean-Paul Schmitt, Arpajon; Renee Gardaix-Luthereau, Cachan, all of France; Robert Naylor; Brenda Costall, both of Addingham, United Kingdom

[73] Assignee: Laboratoires Delagrange Societe D'Applications Pharmacodnymiques, Paris, France

[21] Appl. No.: 454,015

[22] Filed: Dec. 20, 1989

[30] Foreign Application Priority Data

Dec. 20, 1988 [FR] France ................ 88 16764

[51] Int. Cl.$^5$ ............... A61K 31/42; A61K 31/415
[52] U.S. Cl. .................... 514/377; 514/374; 514/385; 514/386; 514/392
[58] Field of Search ............ 514/374, 377, 385, 392, 514/386

[56] References Cited

U.S. PATENT DOCUMENTS

| | | |
|---|---|---|
| 4,210,660 | 7/1980 | Takashima et al. ........... 424/274 |
| 4,835,172 | 5/1989 | Acher et al. ............... 514/392 |
| 4,877,780 | 10/1989 | Vega-Noverola et al. ...... 514/161 |
| 4,914,117 | 4/1990 | Acher et al. ............... 514/377 |

FOREIGN PATENT DOCUMENTS

| | | | |
|---|---|---|---|
| 295350 | 12/1988 | European Pat. Off. ......... 31/415 |
| 3643103 | 6/1987 | Fed. Rep. of Germany ...... 403/12 |
| 2592042 | 6/1987 | France .................... 223/24 |

OTHER PUBLICATIONS

Chemical Abstracts (108:37828a) 1988.
Chemical Abstracts (111:146821a).
Harrington et al., "Metaclopramide—An Updated Review of its Pharmacological Properties and Clinical Use", Drug, vol. 25, pp. 463-464 (1983).
Crawley et al., Pharmacology, Biochemistry and Behavior, vol. 15, pp. 695-699 (1981).
Costall et al., Neuropharmacology, vol. 26, pp. 195-200 (1987).

Primary Examiner—Frederick E. Waddell
Assistant Examiner—K. Weddington
Attorney, Agent, or Firm—Fitzpatrick, Cella, Harper & Scinto

[57] ABSTRACT

The present invention relates to the application of substituted benzamides of formula (I):

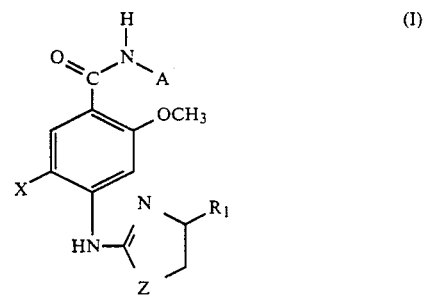

in which:

A is diethylaminoethyl, 1-ethyl-2-pyrrolidinylmethyl or 1-allyl-2-pyrrolidinylmethyl;
$R_1$ is hydrogen or methyl;
X is chlorine or bromine;
Z is —NH— or —O— except when Z is —NH—,
$R_1$ is hydrogen and X is chlorine, and of their pharmacologically acceptable addition salts, as anxiolytics and antipsychotics.

16 Claims, No Drawings

METHOD OF PROVIDING ANXIOLYTIC AND ANTIPSYCHOTIC TREATMENT WITH SUBSTITUTED BENZAMIDES

BACKGROUND OF THE INVENTION

A number of common physical, mental and psychological disorders have been associated with states of psychoneuroses or anxiety. Such states typically result in feelings of apprehension, uncertainty or fear, without apparent stimulus or objectively out of proportion to any apparent cause, and may be associated with physiological changes such as tachycardia, sweating and tremors. Furthermore, an extreme state of anxiety is a common consequence of withdrawal from substances capable of inducing drug dependence, such as alcohol, nicotine and cocaine. In use, such substances produce an anxiolytic effect. However, their chronic use is accompanied by a state of dependence. The sudden interruption of these substances may even exacerbate the intial anxiety, making withdrawal from the substances extremely difficult.

The benzodiazepine-type drugs customarily used in the treatment of anxiety have the disadvantage of inducing, on cessation of treatment, an exacerbation of the anxiety and, therefore, do not constitute effective therapy, for instance, for drug addicts undergoing withdrawal. Accordingly, chemical compounds that can relieve states of psychoneuroses or anxiety have been sought for use as pharmaceutical agents in the treatment of patients. In particular, there has been a need for anxiolytic agents that relieve the anxiety of withdrawal from addictive drug substances.

Schizophrenia is an imbalance that encompasses any of a group of severe emotional disorders, usually of psychotic proportions, characterized by misinterpretation and retreat from reality, delusions, hallucinations, ambivalence, inappropriate affect, and withdrawn, bizarre, or regressive behavior. Accordingly, chemical compounds that can relieve the symptoms including anxiety, characteristic of psychotic disorders such as schizophrenia have also been sought for use as pharmaceutical agents in the treatment of patients.

The present theory of the physiopathology of schizophrenia is that an augmented dopaminergic activity in the medial temporal lobes of the brain is responsible for the dopamine induced hyperactivity characteristic of this disorder. Thus, the antipsychotic drugs currently in use are antidopanminergics.

SUMMARY OF THE INVENTION

The present invention concerns pharmaceutical uses of the compounds represented by the following chemical formula I:

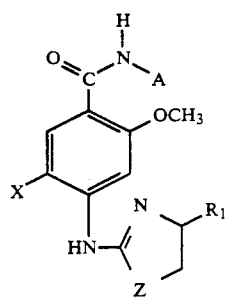

in which:
A is diethylaminoethyl or a group of formula II:

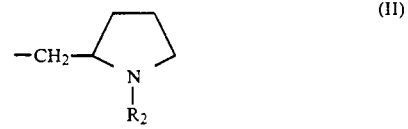

where $R_2$ is ethyl or allyl,
$R_1$ is hydrogen or methyl,
X is chlorine or bromine, and
Z is —NH— or —O—, with the following condition:
that when Z is —NH— and X is chlorine, $R_1$ is methyl,
or any of the pharmacologically acceptable salts, as addition salts, thereof.

The compounds of Formula I, and methods for their preparation, are described in French Patent No. 2,592,042 and U.S. Pat. No. 4,835,172, issued May 30, 1989, the disclosures of which are incorporated herein by reference, as activators of the central nervous system and as antidepressants.

In addition to such properties, it has now been found that the instant compounds possess anxiolytic and antipsychotic properties.

As psychotropic agents, the compounds are distinguished from other methoxybenzamide compounds by the fact that they do not possess antidopaminergic properties. Thus, the compounds are not neuroleptics in the usual sense of the term, as they are not bound to the $D_1$–$D_2$ dopaminergic receptors. They are inactive in the behavior tests customarily performed to test neuroleptics. These results do not suggest that the compounds are tranquilizers or, more specifically, anxiolytic agents and antipsychotic agents. However the compounds have been shown to be potent anxiolytic agents in standard laboratory animals. This has been demonstrated by the two-compartment (dark and light) box test in the mouse. Further tests have demonstrated that the compounds do suppress the hyperactivity induced by a dopamine agonist, amphetamine, perfused in the brain of the rat, more specifically in the nucleus accumbens, thus indicating a utility in the treatment of psychotic disorders, such as schizophrenia.

DETAILED DESCRIPTION OF THE INVENTION

Typical examples of useful compounds within the scope of this invention include:

Compound 1: N-[2-(diethylamino)ethyl]-2-methoxy-4-[(4,5-dihydro-4-methyl-1H-imidazol-2-yl)amino]-5-chlorobenzamide.

Compound 2: N-(1-allyl-2-pyrrolidinylmethyl)-2-methoxy-4-[(4,5-dihydro-4-methyl-1H-imidazol-2-yl)amino]-5-chlorobenzamide.

Compound 3: N-[2-(diethylamino)ethyl]-2-methoxy-4-[(4,5-dihydro-4-methyl-1H-imidazol-2-yl)amino]-5-bromo-benzamide.

Compound 4: N-(1-ethyl-2-pyrrolidinylmethyl)-2-methoxy-4-[(4,5-dihydro-4-methyl-1H-imidazol-2-yl)amino]-5-bromobenzamide.

Compound 5: N-(1-ethyl-2-pyrrolidinylmethyl)-2-methoxy-4-[(4,5-dihydro-4-methyl-1H-imidazol-2-yl)amino]-5-chlorobenzamide.

Compound 6: N-[2-(diethylamino)ethyl]-2-methoxy-4-[(4,5-dihydro-1H-imidazol-2-yl)amino]-5-bromobenzamide.

Compound 7: N-[2-(diethylamino)ethyl]-2-methoxy-4-[(4,5-dihydro-2-oxazolyl)amino]-5-chlorobenzamide.

A very thorough study of the compounds of the invention in standard laboratory animals has demonstrated that they possess unexpected properties. The protocols used and the test results obtained are described hereinafter.

The two compartment box test was conducted in mice to evaluate anxiolytic activity. This test is based on a natural aversion of mice to light. The apparatus used is a box containing two compartments, one of which is dark (labeled "black compartment" in the Table 1) and the other illuminated (labeled "white compartment" in Table 1). The apparatus is designed to allow the animal to choose between staying in either of the two compartments. Under normal conditions, the mice avoid light and usually remain in the dark compartment. Under the influence of an anxiolytic agent, however, exploration of the illustrated compartment predominates.

The test consists of placing each mouse in the center of the illuminated compartment and observing the animal's behavior by video system for 5 minutes. The number of exploratory rearings and the number of displacements (the crossing of lines traced on the floor of each compartment constitute "passages") are then recorded for each compartment.

An anxiolytic effect induced by a drug, such as diazepam, is characterized by an increase in the number of exploratory rearings and in the number of passages into the illuminated compartment.

The compounds of the invention were injected subcutaneously at variable doses, each dose being administered to a group of 5 mice. The observation of each animal took place 40 minutes after administration of the product, and the results were compared with the results obtained with a control group which received only an inert vehicle.

The results obtained are collated in Table 1.

It is apparent that the compounds of the invention have considerable anxiolytic activity, which is manifested in a significant increase in the number of exploratory rearings and of shifts from place to place in the illuminated compartment, an increase in the time elapsing before moving from the illuminated compartment to the dark compartment and a decrease in the residence time in the dark compartment, at subcutaneous doses of 0.1 mg/kg –1 mg/kg. The compounds 1 and 2 even manifest this activity at 0.01 mg/kg and above, and the compound 4 at 0.0001 mg/kg and above.

Tests were conducted to measure the antipsychotic activity of the compounds of the invention. In particular, the hyperactivity induced in rats by the perfusion of amphetamine into the nucleus accumbens was evaluated. This test consists in determining the effect of the compounds of the invention on hyperactivity produced in rats by the injection of amphetamine into the nucleus accumbens. Hyperactivity was induced by injecting 20 μg of amphetamine bilaterally into the nucleus accumbens. The compounds of the invention were administered subcutaneously at doses of 1 mg/kg and 10 mg/kg, 40 minutes before the injection of amphetamine. For each dose of test product, a group of 5 animals was used. A group treated only with amphetamine and a reference group which received only an inert vehicle comprised 10 animals.

Immediately after the injection of amphetamine, the rats were placed in individual cages equipped with photoelectric cells. Motor activity, characterized by the number of shifts from place to place in these cages, was determined by the number of interruptions of a light beam striking these cells. The measurements were made during the 80 minutes following the injection of amphetamine. The results, expressed as the number of shifts from place to place per 10-minute period, are collated in Table 2.

It is apparent that the compounds of the invention, at subcutaneous doses of 1 and 10 mg/kg, antagonize hyperactivity induced by the injection of amphetamine into the nucleus accumbens. This action is highly predictive of antipsychotic properties.

TABLE 1

| Compound administered in mg/kg | White Compartment rearings/ 5 min | White Compartment transits/ 5 min | Black compartment rearings/ 5 min | Black compartment transits/ 5 min | % time in black compartment | Delay white → black (sec) |
|---|---|---|---|---|---|---|
| Vehicle (1) | 27 | 37 | 67 | 84 | 56 | 9 |
| Compound 1 | | | | | | |
| 0.01 | 57 | 77 | 16 | 37 | 36 | 19 |
| 0.1 | 73 | 79 | 14 | 23 | 27 | 22 |
| Compound 6 | | | | | | |
| 0.1 | 40 | 48 | 39 | 50 | 27 | 13 |
| Compound 7 | | | | | | |
| 0.1 | 69 | 68 | 16 | 16 | 27 | 24 |
| Vehicle (2) | 22 | 36 | 72 | 91 | 52 | 11 |
| Compound 2 | | | | | | |
| 0.01 | 43 | 51 | 27 | 30 | 49 | 18 |
| 0.1 | 83 | 80 | 20 | 25 | 29 | 20 |
| Compound 3 | | | | | | |
| 0.1 | 97 | 104 | 18 | 18 | 30 | 23 |
| Compound 4 | | | | | | |
| 0.0001 | 73 | 82 | 19 | 21 | 27 | 23 |
| 0.01 | 82 | 83 | 15 | 20 | 31 | 22 |
| 0.1 | 78 | 99 | 16 | 24 | 34 | 38 |
| Compound 5 | | | | | | |
| 1 | 65 | 89 | 14 | 19 | 32 | 23 |
| 10 | 68 | 80 | 15 | 16 | 32 | 22 |

The compounds of the invention were also subjected to a study of acute toxicity when injected intravenously in male mice and female mice, which enabled the median lethal doses ($LD_{50}$) to be determined.

The following results were obtained:

| Compound | $LD_{50}$ I.V. (mg/kg) Male Mice | $LD_{50}$ I.V. (mg/kg) Female Mice |
|---|---|---|
| Compound 1 | 19.5 (17.5–21.8) | 24.0 (21.6–26.6) |
| Compound 2 | 42.0 (35.1–50.2) | 42.0 (35.1–50.2) |
| Compound 3 | 22.0 (19.5–24.8) | 24 (21.1–27.2) |
| Compound 4 | 15.5 (13.1–18.3) | 18.0 (15.7–20.7) |
| Compound 6 | 103 (91–116) | 118 (106–132) |

The results obtained are compatible with use of the compounds of the invention as drugs.

By way of illustration only, the compounds may be formulated in tablet dosage form as shown below. As the formulation is provided for illustrative purposes only, it is understood that the invention is not restricted or limited thereto, as the scope of the invention is defined and restricted or limited solely as set forth in the appended claims.

N-[2-(diethylamino)-ethyl]-2-methoxy-4-[(4,5-dihydro-4-methyl-1H-       100 mg

-continued

| | |
|---|---|
| imidazol-2-yl)-amino]-5-chlorobenzamide | |
| dried starch | 20 mg |
| lactose | 100 mg |
| methylcellulose 1500 cps | 1.5 mg |
| levilite | 10 mg |
| magnesium stearate | 4 mg |

TABLE 2

| Time (min.) | Motor activity (shifts from place to place/10 minutes) | | | | | |
|---|---|---|---|---|---|---|
| | Amphetamine (20 μg) | Vehicle | Compound 1 | | Compound 4 | |
| | | | 1 mg/kg | 10 mg/kg | 1 mg/kg | 10 mg/kg |
| 10 | 31 ± 4 | 32 ± 3 | 49 ± 9 | 27 ± 4 | 34 ± 8 | 38 ± 7 |
| 20 | 48 ± 5* | 29 ± 3 | 35 ± 3 | 27 ± 6 | 60 ± 13* | 8 ± 1.4 |
| 30 | 66 ± 7* | 18 ± 3 | 45 ± 8* | 13 ± 3 | 40 ± 10* | 9 ± 3 |
| 40 | 59 ± 7* | 9 ± 2 | 40 ± 8* | 11 ± 2 | 38 ± 13* | 11 ± 1.6 |
| 50 | 36 ± 5* | 6 ± 1.4 | 11 ± 3 | 8 ± 2 | 37 ± 10* | 5 ± 1 |
| 60 | 29 ± 4* | 3 ± 1 | 12 ± 2 | | 16 ± 2* | 2 ± 1 |
| 70 | 19 ± 3 | | 8 ± 1 | | 8 ± 3 | |
| 80 | 8 ± 3 | | | | 4 ± 2 | |

In Table 1, S.E.M. <12.6%; n = 5; p < 0.05 to p < 0.001. All the results relating to the treated batches are significant with respect to the results for the controls.
In Table 2, the asterisk (*) denotes p < 0.05 to p < 0.001 and the cross ( ) denotes p < 0.01.

What is claimed is:

1. A method of treating anxiety of psychotic disorders which comprises administering to a psychotic patient exhibiting anxiety, a therapeutically effective amount of a compound of the general formula (I):

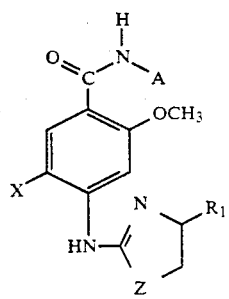

in which:
A is diethylaminoethyl or a group of formula II:

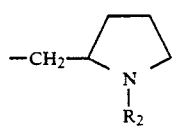

where $R_2$ is ethyl or allyl;
$R_1$ is hydrogen or methyl;
X is chlorine or bromine, and
Z is —NH—OR—O—
with the following condition:
when Z is —NH— and X is chlorine, $R_1$ is methyl
and their pharmacologically acceptable salts.

2. The method according to claim 1 employing N-[2-(diethylamino)ethyl]-2-methoxy-4-[(4,5-dihydro-4-methyl-1H-imidazol-2-yl)amino]-5-chlorobenzamide.

3. The method according to claim 1 employing N-(1-allyl-2-pyrrolidinylmethyl)-2-methoxy-4-[(4,5-dihydro-4-methyl-1H-imidazol-2-yl)amino]-5-chlorobenzamide.

4. The method according to claim 1 employing N-[2-(diethylamino)ethyl]-2-methoxy-4-[(4,5-dihydro-4-methyl-1H-imidazol-2-yl)amino]-5-bromobenzamide.

5. The method according to claim 1 employing N-(1-ethyl-2-pyrrolidinylmethyl)-2-methoxy-4-[(4,5-dihydro-4-methyl-1H-imidazol-2-yl)amino]-5-bromobenzamide.

6. The method according to claim 1 employing N-[2-(diethylamino)ethyl]-2-methoxy-4-[(4,5-dihydro-1H-imidazol-2-yl)amino]-5-bromobenzamide.

7. The method according to claim 1 employing N-[2-(diethylamino)ethyl]-2-methoxy-4-[(4,5-dihydro-2-oxazolyl)amino]-5-chlorobenzamide.

8. The method according to claim 1 employing N-(1-ethyl-2-pyrrolidinylmethyl)-2-methoxy-4-[(4,5-dihydro-4-methyl-1H-imidazol-2-yl)amino]-5-chlorobenzamide.

9. A method of treating schizophrenia which comprises administering to a patient exhibiting the psychotic characteristics of schizophrenia, a therapeutically effective amount of a compound formula (I) as follows:

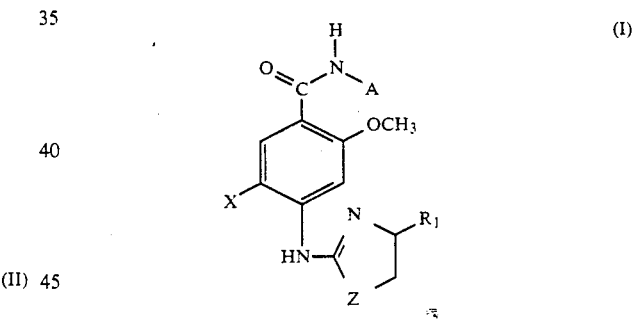

in which:
A is diethylaminoethyl or a group of formula II:

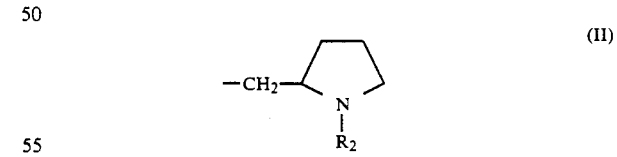

where $R_2$ is ethyl or allyl;
$R_1$ is hydrogen or methyl;
X is chlorine or bromine, and
Z is —NH—OR—O—
with the following condition:
when Z is —NH— and X is chlorine, $R_1$ is methyl
and their pharmacologically acceptable salts.

10. The method according to claim 9 employing N-[2-(diethylamino)ethyl]-2-methoxy-4-[(4,5-dihydro-4-methyl-1H-imidazol-2-yl)amino]-5-chlorobenzamide.

11. The method according to claim 9 employing N-(1-allyl-2-pyrrolidinylmethyl)-2-methoxy-4-[(4,5-dihydro-4-methyl-1H-imidazol-2-yl)amino]-5-chlorobenzamide.

12. The method according to claim 9 employing N-[2-(diethylamino)ethyl]-2-methoxy-4-[(4,5-dihydro-4-methyl-1H-imidazol-2-yl)amino]-5-bromobenzamide.

13. The method according to claim 9 employing N-(1-ethyl-2-pyrrolidinylmethyl)-2-methoxy-4-[(4,5-dihydro-4-methyl-1H-imidazol-2-yl)amino]-5-bromobenzamide.

14. The method according to claim 9 employing N-[2-(diethylamino)ethyl]-2-methoxy-4-[(4,5-dihydro-1H-imidazol-2-yl)amino]-5-bromobenzamide.

15. The method according to claim 9, employing N-[2-(diethylamino)ethyl]-2-methoxy-4-[(4,5-dihydro-2-oxazolyl)amino]-5-chlorobenzamide.

16. The method according to claim 9 employing N-(1-ethyl-2-pyrrolidinylmethyl)-2-methoxy-4-[(4,5-dihydro-4-methyl-1H-imidazol-2-yl)amino]-5-chlorobenzamide.

* * * * *

UNITED STATES PATENT AND TRADEMARK OFFICE
CERTIFICATE OF CORRECTION

PATENT NO. : 5,086,066
DATED : February 4, 1992
INVENTOR(S) : JACQUES ACHER, ET AL.   Page 1 of 2

It is certified that error appears in the above-identified patent and that said Letters Patent is hereby corrected as shown below:

COLUMN 1

Line 20, "intial" should read --initial--.
Line 40, "symptoms" should read --symptoms,--.
Line 47, "dopamine induced" should read --dopamine-induced--.
Line 49, "antidopanminergics" should read --antidopaminergics--.

COLUMN 2

Line 61, "bromo-benzamide" should read --bromobenzamide--.

COLUMN 3

Line 22, "illustrated" should read --illuminated--.

COLUMN 5

TABLE 2, Move "Table 2" to Column 4, Line 41; "8 ± 1.4" should read --8 ± 1.4†--; and "cross ( )" should read --cross (†)--.
Line 54, "—NH—OR—O—" should read -- —NH— or —O— --.

UNITED STATES PATENT AND TRADEMARK OFFICE
CERTIFICATE OF CORRECTION

PATENT NO. : 5,086,066
DATED : February 4, 1992
INVENTOR(S) : JACQUES ACHER, ET AL.

Page 2 of 2

It is certified that error appears in the above-identified patent and that said Letters Patent is hereby corrected as shown below:

COLUMN 6

Line 60, "—NH—OR—O—" should read -- —NH— or —O— --.

Signed and Sealed this

Fourth Day of May, 1993

Attest:

MICHAEL K. KIRK

*Attesting Officer*    *Acting Commissioner of Patents and Trademarks*